(12) United States Patent
Katoh et al.

(10) Patent No.: US 7,377,910 B2
(45) Date of Patent: May 27, 2008

(54) REAGENT INJECTION DEVICE

(75) Inventors: Osamu Katoh, Kyoto (JP); Masashi Momota, Kamakura (JP); Tomihisa Kato, Anjo (JP)

(73) Assignees: Osamu Katoh, Kyoto (JP); Asahi Intecc Co., Ltd., Aichi (JP)

( * ) Notice: Subject to any disclaimer, the term of this patent is extended or adjusted under 35 U.S.C. 154(b) by 115 days.

(21) Appl. No.: 10/793,351

(22) Filed: Mar. 4, 2004

(65) Prior Publication Data

US 2004/0176726 A1    Sep. 9, 2004

(30) Foreign Application Priority Data

Mar. 6, 2003    (JP)    ............................ 2003-059868

(51) Int. Cl.
*A61M 5/178*    (2006.01)
(52) U.S. Cl. ................................ 604/164.13
(58) Field of Classification Search ................ 604/190, 604/164.01, 164.06, 164.13, 164.12, 166.01, 604/170.03, 170.02, 101.05, 272, 96.01
See application file for complete search history.

(56) References Cited

U.S. PATENT DOCUMENTS

| | | | |
|---|---|---|---|
| 3,833,003 A | 9/1974 | Taricco | |
| RE31,873 E * | 4/1985 | Howes | ........................ 128/674 |
| 4,578,061 A | 3/1986 | Lemelson | |
| 4,601,701 A | 7/1986 | Mueller, Jr. | |
| 4,769,005 A | 9/1988 | Ginsburg et al. | |
| 4,808,156 A | 2/1989 | Dean | |
| 5,059,177 A | 10/1991 | Towne et al. | |
| 5,190,528 A | 3/1993 | Fonger et al. | |
| 5,209,741 A | 5/1993 | Spaeth | |
| 5,261,889 A | 11/1993 | Laine et al. | |
| 5,263,932 A | 11/1993 | Jang | |
| 5,342,301 A | 8/1994 | Saab | |
| 5,354,279 A * | 10/1994 | Hofling | .................. 604/164.12 |
| 5,413,581 A | 5/1995 | Goy | |
| 5,419,777 A | 5/1995 | Hofling | |
| 5,464,395 A * | 11/1995 | Faxon et al. | ............ 604/103.02 |
| 5,569,184 A | 10/1996 | Crocker et al. | |
| 5,702,384 A | 12/1997 | Umeyama et al. | |
| 5,797,869 A * | 8/1998 | Martin et al. | .................. 604/43 |
| 5,916,194 A * | 6/1999 | Jacobsen et al. | ......... 604/96.01 |
| 6,068,610 A | 5/2000 | Ellis et al. | |
| 6,068,638 A | 5/2000 | Makower | |
| 6,135,976 A | 10/2000 | Tachibana et al. | |
| 6,217,554 B1 * | 4/2001 | Green | .................... 604/164.01 |
| 6,248,122 B1 | 6/2001 | Klumb et al. | |
| 6,283,947 B1 | 9/2001 | Mirzaee | |

(Continued)

FOREIGN PATENT DOCUMENTS

EP    1070513 A1    7/2000

(Continued)

*Primary Examiner*—Nicholas D. Lucchesi
*Assistant Examiner*—Christopher D Koharski
(74) *Attorney, Agent, or Firm*—Knobbe, Martens, Olson & Bear LLP

(57) ABSTRACT

Embodiments of the present invention relate to an injection devices that inject a specified reagent with cells into lesions and other areas of body tissue. Particular embodiments comprise a main tube with a projection hole on its exterior, an axially-moveable needle tube with a needle at its tip, a reagent supplier configured to supply a specified reagent into the needle tube, and axially-moveable guide wires.

16 Claims, 11 Drawing Sheets

U.S. PATENT DOCUMENTS

| | | |
|---|---|---|
| 6,302,870 B1 | 10/2001 | Jacobsen et al. |
| 6,355,060 B1 * | 3/2002 | Lenker et al. ............. 623/1.34 |
| 6,375,615 B1 | 4/2002 | Flaherty et al. |
| 6,436,090 B1 | 8/2002 | Sanchez et al. |
| 6,458,098 B1 | 10/2002 | Kanesaka |
| 6,461,296 B1 | 10/2002 | Desai |
| 6,494,905 B1 | 12/2002 | Zedler et al. |
| 6,524,302 B2 | 2/2003 | Kelly |
| 6,544,230 B1 | 4/2003 | Flaherty et al. |
| 6,547,767 B1 | 4/2003 | Moein |
| 6,689,099 B2 | 2/2004 | Mirzaee |
| 6,692,466 B1 | 2/2004 | Chow et al. |
| 6,706,017 B1 | 3/2004 | Dulguerov |
| 6,884,258 B2 | 4/2005 | Vardi et al. |
| 6,926,692 B2 * | 8/2005 | Katoh et al. ........... 604/164.01 |
| 2001/0011180 A1 | 8/2001 | Fitzmaurice et al. |
| 2001/0025134 A1 | 9/2001 | Bon et al. |
| 2002/0055733 A1 * | 5/2002 | Wilson ....................... 604/528 |
| 2002/0072706 A1 | 6/2002 | Hiblar et al. |
| 2003/0040712 A1 | 2/2003 | Ray et al. |
| 2003/0171714 A1 | 9/2003 | Katoh et al. |
| 2004/0176726 A1 | 9/2004 | Katoh et al. |

FOREIGN PATENT DOCUMENTS

| | | |
|---|---|---|
| WO | WO 99/44539 | 9/1999 |

* cited by examiner

REAGENT INJECTION DEVICE

BACKGROUND OF THE INVENTION

The present application claims priority under 35 U.S.C. § 119 to Japanese Patent Application No. 2003-059868, filed on Mar. 6, 2003, the disclosure of which is incorporated herein by reference in its entirety.

1. Field of the Invention

The present invention relates to reagent injection devices. More particularly, this invention relates to an injection device that injects a specified reagent (which need not but may contain cells, chemicals, etc.) into lesions and other areas of body tissue.

2. Description of the Related Art

In various medical procedures, catheters and other medical apparatuses have traditionally been inserted into components of the cardiovascular system, the gastrointestinal tract, the urinal tract, and other tubular organs of the human body. Recently, as illustrated in Japanese Patent Application Laid-open Nos. 2001-104487 and 2001-299927, reagent injection catheters have been used to inject specific reagents into lesions of body tissues.

Reagent injection catheters of the prior art typically consist of a tubular catheter body, a needle tube, and a needle. The needle usually projects out of the catheter body and pierces various areas of body tissue. However, conventional reagent injection devices are generally equipped with a long, flexible needle tube, which can become bent or retracted upon contact with the relatively hard lesions of body tissue. Consequently, it can be difficult to insert the needle to a desired depth or to a specific position in lesions of body tissues.

SUMMARY OF THE INVENTION

Preferred embodiments of the present invention comprise reagent injection devices that reliably allow a needle of a needle tube to pierce through tissues and lesions of tissues to a desired depth with a desired position.

Particularly preferred embodiments of the reagent injection device of the present invention comprise a main tube comprising a tubular body which is insertable into the human body. The main tube further comprises a projection hole on its exterior and a needle tube which preferably comprises a flexible tube with a needle at its tip. The needle tube is preferably inserted into the main tube and is movable in the axial direction, which causes the needle to project out of the projection hole of the main tube.

Embodiments of the device further comprise a reagent supplier configured to supply a specified reagent into the needle tube. The main tube can be inserted into the body, and the needle of the needle tube is preferably projected out of the projection hole of the main tube and caused to pierce a specified tissue in the body. A reagent is then delivered from the reagent supplier through the needle tube and is injected into the body tissue.

In preferred embodiments, the reagent injection device further comprises a first guide wire that is inserted into the main tube. The first guide wire is preferably axially movable and extends through a tip aperture provided at the front of the main tube, as viewed in the direction of its insertion into the body. Preferred embodiments also comprise a second guide wire that is inserted into the main tube. The second guide wire is preferably axially movable and extends through a side hole that opens in the direction orthogonal to both the opening direction of the projection hole and the opening direction of the aforementioned tip aperture.

In preferred embodiments, the extension-direction vectors of the first and second guide wires cross each other. Preferred embodiments of the present invention. ensure that the tip of the needle of the needle tube can be projected out of the projection hole of the tubular wall of the main tube, in a direction virtually orthogonal to the plane that includes the extension-direction vectors of the first guide wire and second guide wire, along with the axial-direction movement of the needle tube inside the main tube. This projection of the needle is achievable when the actual extension directions of the first and second guide wires do not cross each other but are displaced from each other.

In preferred embodiments of the reagent injection device, the plane formed by the first and second guide wires will virtually approximate the surface of the lesion of body tissue. This approximation can preferably occur when the first and second guide wires are positioned to extend out along the surface of the lesion of body tissue, by means, for example, of inserting the guide wires into a blood vessel running over the body tissue, as the needle of the needle tube is pierced into the lesion of body tissue. In this case, the needle will preferably project out of the projection hole in the main tube in a direction perpendicular to the surface of the lesion. This preferably enables the needle to pierce at specified position of the body tissue lesion.

Furthermore, when the needle is pierced into the body tissue, a majority of the reactive force generated as the needle progresses into the body tissue will act in a direction perpendicular to the surface of the body tissue. For example, the force will act in a direction perpendicular to the plane that includes the respective extension directions of the first and second guide wires, which is also the direction opposite to the progressing direction of the needle. Therefore, the reactive force will be divided and each component force can preferably be sufficiently and reliably supported by the first and second guide wires. This configuration preferably allows the needle to progress into the body tissue in a very smooth and reliable manner.

For the above reasons, a reagent injection device based on the present invention allows the needle of the needle tube to reliably pierce through to a desired depth at a specified position in the desired lesion of body tissue, even when the lesion is relatively hard. As a result, the effectiveness of the treatment or procedure of injecting a specified reagent into the lesion can be further increased.

One preferred embodiment of the reagent injection device comprises, within the aforementioned main tube, a first lumen that opens toward the outside through the tip aperture in the main tube. The device further comprises a second lumen that opens to the outside through the side hole, and a third lumen that opens to the outside through the projection hole. The first guide wire is preferably inserted into the first lumen and is preferably movable in the axial direction. The second guide wire is preferably inserted into the second lumen and is preferably movable in the axial direction. The needle tube is preferably inserted into the third lumen so that it is moveable in the axial direction. This configuration allows the first and second guide wires and needle tube to move smoothly in the axial direction within the main tube, thereby enabling the applicable medical technique to be performed more smoothly.

Another preferred embodiment of a reagent injection device based on the present invention allows the first lumen to open sideways through an insertion hole provided in the tubular wall at the rear end of the main tube, as viewed in the direction of its insertion into the body. Furthermore, this embodiment allows the first guide wire to be inserted into the first lumen through the insertion hole, while simultaneously allowing the second lumen to open to the rear through a rear-end aperture at the rear of the main tube. This embodiment preferably allows the second guide wire to be inserted into the second lumen through the rear-end aperture. By using this configuration, the first and second guide wires can each bend at a single location. The first guide wire can bend at the insertion position of the first lumen, and the second guide wire can bend at the extension position out of the second lumen. This configuration minimizes the bending of each guide wire. Instead of the first and second guide wires bending at the two locations of the insertion and extension positions into and out of the first and second lumens, each guide wire can preferably receive a favorably smaller slide resistance as it moves inside of each lumen. This results in an enhanced usability and operability of the reagent injection device.

An additional preferred embodiment of the present reagent injection device comprises a first lumen and second lumen provided inside of the main tube. The plane that includes the center axes of the respective lumens preferably lies orthogonal to the opening direction of the projection hole. In such reagent injection devices, the needle at the tip of the needle tube can preferably be more reliably projected out of the projection hole in a direction orthogonal to the plane that includes the extension directions of the first and second guide wires. This preferably causes a majority of the reactive force, generated as the needle progresses into the body tissue, to be sufficiently and reliably supported by the first and second guide wires. Consequently, the needle will progress into the body tissue in a smoother and more reliable manner.

Yet another preferred embodiment comprises a third lumen positioned inside of the main tube so that the center of the projection hole is preferably positioned in the plane that includes the center axes of the third lumen and the main tube. This configuration allows the needle tube to be preferably positioned inside of the main tube in a more balanced manner, thus allowing smoother performance of the applicable medical technique.

In an embodiment of the reagent injection device based on the present invention, it is advantageous to position the aforementioned third lumen inside of the main tube in so that its center axis corresponds to the center axis of the main tube. Moreover, the first and second lumens are positioned inside of the main tube, on both sides of the third lumen, in such a way that their center axes are positioned in the same plane that includes the center axis of the third lumen. This configuration preferably causes the distance between the first and second lumens to be maximized, thereby increasing the distance between the first and second guide wires extending out of the first and second lumens. Consequently, a majority of the reactive force generated as the needle progresses into the body tissue can be sufficiently and reliably supported by the first and second guide wires.

Another preferred embodiment of the present invention comprises an expandable and/or shrinkable balloon attached to the exterior of the main tube. The embodiment preferably comprises a fourth lumen, that supplies a liquid for expanding the balloon, positioned within the main tube so that the center of the aforementioned projection hole is positioned in the same plane that includes the center axes of the fourth lumen and main tube. In a reagent injection device comprising this configuration, the main tube can preferably be fixed in a specified position in the blood vessel into which the main tube is inserted. This is preferably achieved by expanding the balloon inside of the blood vessel. This allows the needle to project out of the main tube and pierce a desired location of body tissue in a more reliable manner. The fourth lumen that supplies the liquid for expanding the balloon can preferably be positioned inside of the main tube in a more balanced manner. As a result, the applicable medical technique using the reagent injection device can be performed more smoothly.

In preferred embodiments, a guide surface is provided in the main tube that guides the needle into the projection hole by means of the frictional contact created by the needle and the axial movement of the needle tube. The guide surface is preferably formed with a convex pattern that curves in the opening direction of the projection hole toward the front of the main tube, as viewed in the direction of its insertion into the body. This configuration allows for a smoother projection of the needle out of the main tube, thus enabling smoother performance of the applicable medical technique.

In further embodiments, the needle at the tip of the needle tube preferably comprises a curved shape corresponding to the convex guide surface as formed inside the main tube. Consequently, the needle tube can preferably be caused to deform in a manner creating a deeper curve by combining the convex curved pattern of the guide surface and the curved shape at the tip of the aforementioned needle tube. The convex curved pattern of the guide surface and the curved shape at the tip of the needle tube are combined when the needle of the needle tube projects out of the projection hole in the main tube in a direction orthogonal to the plane that includes the extension directions of the first and second guide wires. This configuration preferably causes the needle tube to curve further and enables projection near the projection hole, which facilitates identification of the position of the tip of the needle tube through the projection hole. The needle tube preferably projects out of the projection hole at an angle closer to the right angle with respect to the axial direction of the main tube, which results in an increase in the component force that acts in a direction perpendicular to the axial direction of the main tube when the needle tube progresses into a desired location in the lesion of body tissue. Consequently, the needle tube can be inserted more smoothly into a desired location in the lesion of body tissue.

Another particularly preferred embodiment of the present invention comprises a flexible reagent injection device that comprises a main tube inserted into the body, a first axially moveable guide wire that is inserted into the main tube, a second guide wire that is inserted into the main tube and that can be extended out of the main tube and moved back and forth in a direction crossing with the first guide wire, an axially moveable needle tube that is inserted into the main tube, and a reagent supplier configured to supply reagent through the aforementioned needle tube. The needle tube is preferably formed to project out of the main tube in a direction virtually orthogonal to the plane that includes the respective extension-direction vectors of the first and second guide wires. The needle tube preferably projects out of the main tube in a direction virtually orthogonal to the plane that includes the respective extension-direction vectors of the first and second guide wires, so that the tip of the needle tube can reliably and smoothly be pierced and progressed into a specified position in the lesion of a body tissue. Additionally, a majority of the reactive force that is generated in the direction opposite to the needle-progressing direction in the lesion, when the tip of the needle tube progresses into the lesion of body tissue, will be sufficiently and reliably supported by the first and second guide wires. This allows the tip of the needle tube to progress into the lesion of body tissue in a smooth and reliable manner. Therefore, in this preferred embodiment the needle of the needle tube can be pierced in a reliable manner through to a desired depth at a specified position in the targeted lesion of body tissue, even when the lesion is hard. As a result, the effectiveness of the treatment or procedure of injecting a specified reagent into the targeted lesion of tissue can be significantly increased.

For purposes of summarizing the invention and the advantages achieved over the related art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the detailed description of the preferred embodiments which follow.

BRIEF DESCRIPTION OF THE DRAWINGS

These and other features of this invention will now be described with reference to the drawings of preferred embodiments which are intended to illustrate and not to limit the invention.

DETAILED DESCRIPTION OF THE PREFERRED EMBODIMENT

Figure 1:
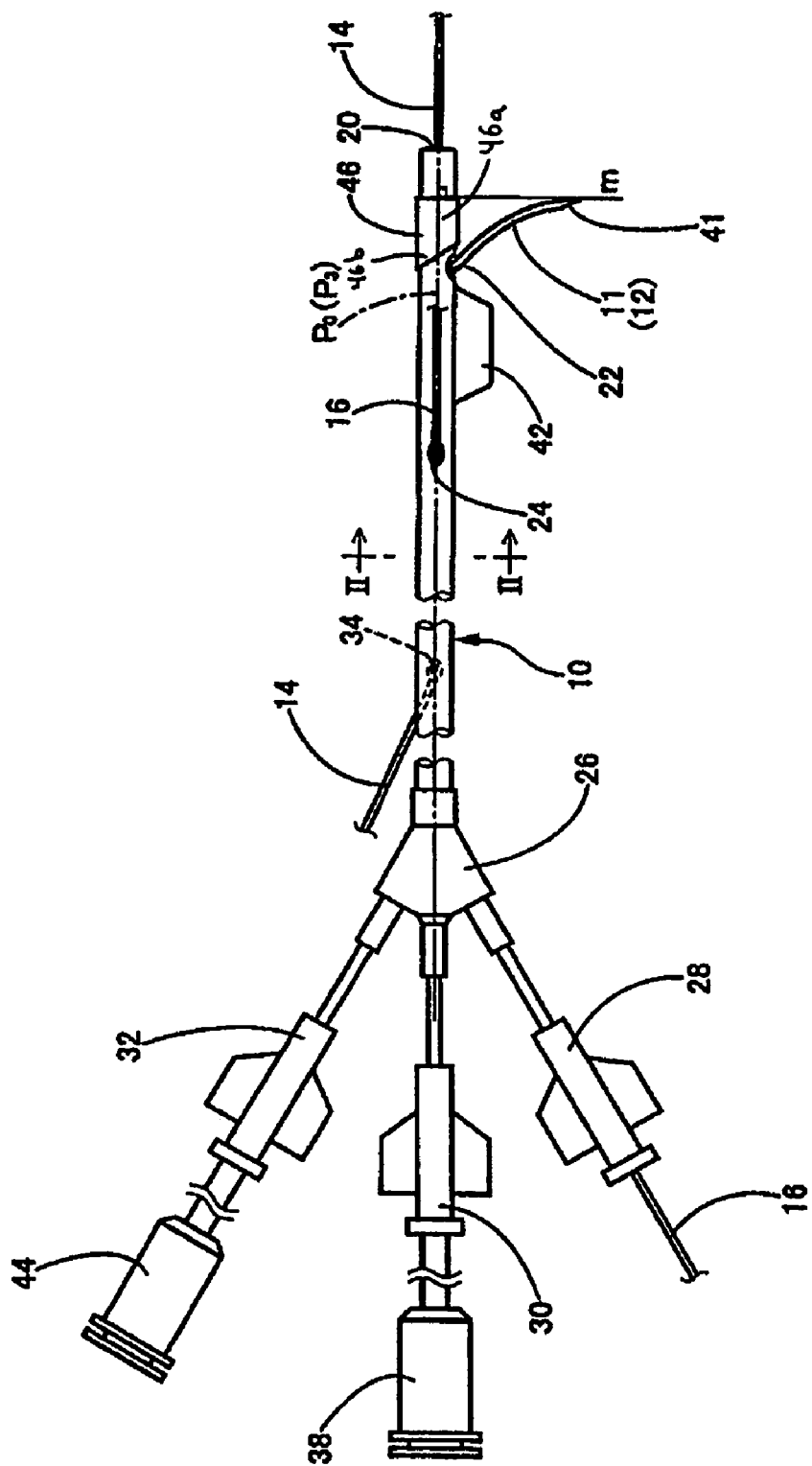
FIG. 1 shows a schematic front view of a preferred reagent injection catheter of the present invention.

The structures of reagent injection devices embodied by the present invention are explained below in detail by referring to the drawings, in order to further elaborate on the present invention.

Figure 2:
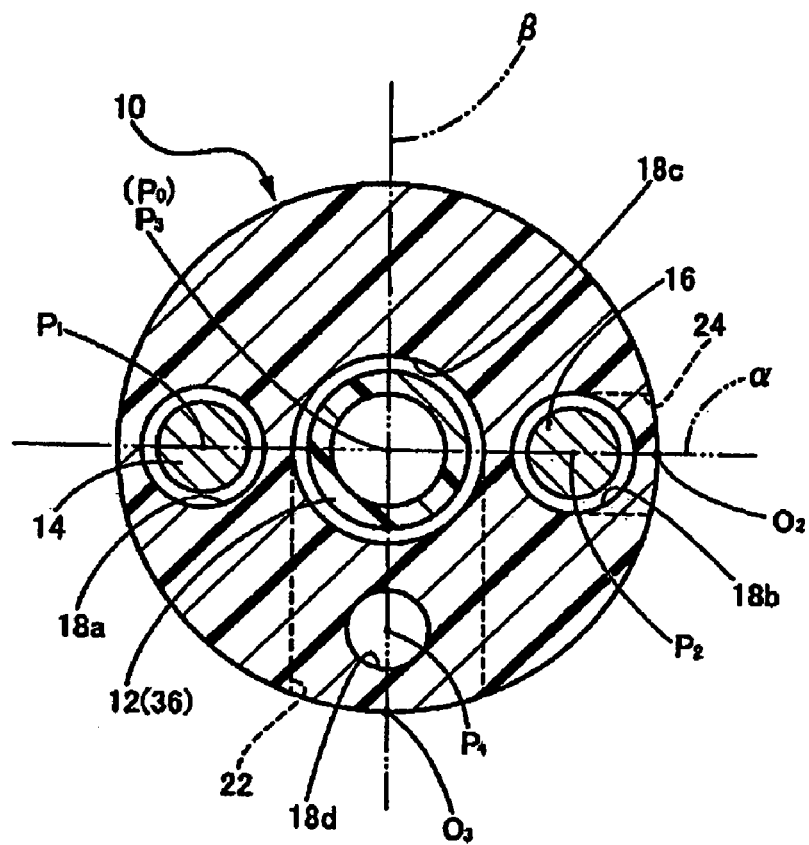
FIG. 2 shows an enlarged cross-sectional view of line II-II of FIG. 1.

FIGS. 1 and 2 show a front and cross sectional view, respectively, of a preferred embodiment of a reagent injection device of the present invention. FIGS. 1 and 2, show a catheter body (10), or main tube, comprising a long tubular body. There is provided a needle tube (12) comprising a needle (11) at its tip, a first guide wire (14) and a second guide wire (16), each of which are inserted into the catheter body and movable in their respective axial directions.

The catheter body (10) preferably has a thickness (approximately 2.0 mm in diameter) and length that allows the catheter to be preferably inserted into the blood vessels extending from the thighs or wrists to the heart in the human body at any point over their entire lengths. The catheter body (10) preferably comprises flexible, tubular inner and outer layers comprising a specific resin, which in some preferred embodiments comprises sandwiching stainless wires. This construction ensures both appropriate stiffness and flexibility to enable smooth insertion into a winding blood vessel. Other preferred embodiments comprise various materials with desired elasticity known to those skilled in the art that could be used to construct such a catheter body (10), such as polyamide and other composite resin materials, Ni—Ti alloy and other ultra-elastic alloy materials, and stainless steel and other metals.

The catheter body (10) preferably further contains four independent lumens, from first through fourth (18a through 18d), which preferably have different diameters and extend continuously in the longitudinal direction.

Of the four lumens (18a through 18d), the first and second lumens (18a, 18b) preferably have the same diameter, which is smaller than the third lumen (18c) but larger than the fourth lumen (18d). The third lumen (18c) preferably has the largest diameter, and the fourth lumen (18d) has the smallest diameter. The first and second lumens (18a, 18b) are preferably arranged in such a way that the center axis ($P_0$) of the catheter body (10) is positioned in the plane ($\alpha$) (indicated by the two-dot chain line in FIG. 2) that includes the center axes ($P_1$, $P_2$) of the first and second lumens (18a, 18b). In accordance with preferred embodiments, the third lumen (18c) is arranged in such a way that its center axis ($P_3$) corresponds to the center axis ($P_0$) of the catheter body (10) and is positioned at the center between the first lumen (18a) and second lumen (18b). Furthermore, the fourth lumen (18d) is preferably arranged in such a way that the plane ($\beta$) (indicated by the two-dot chain line in FIG. 2) that includes its center axis ($P_4$) and the center axis ($P_3$) of the third lumen (18c) lies orthogonal to the plane ($\alpha$) that includes the center axes ($P_1$, $P_2$) of the first and second lumens (18a, 18b).

The catheter body (10) containing these four lumens (18a through 18d) preferably comprises a tip aperture (20) that opens in the axial direction at the tip of the front end (right side in FIG. 1) as viewed in the insertion direction into the blood vessel. In addition, a projection hole (22) that opens to the side through the tubular wall is preferably formed in the catheter body (10) at a position slightly to the rear of the tip of its front end. Furthermore, a side hole (24) that penetrates through the tubular wall is preferably provided at a position further to the rear of the projection hole (22), at the front end of the catheter body (10).

Figure 3:
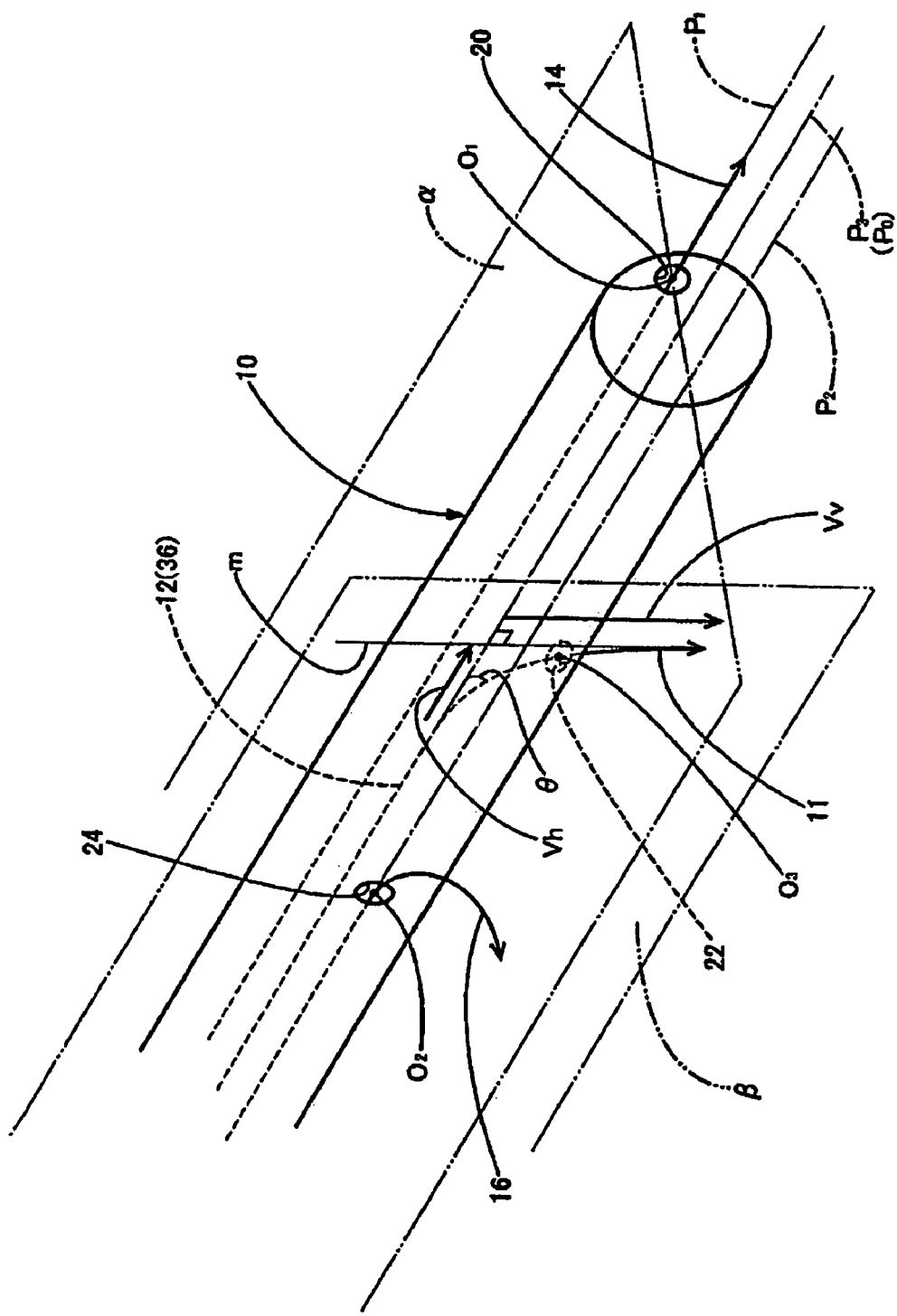
FIG. 3 shows a close up view of the positions of the center axes of the needle tube and first/second guide wires inserted into the catheter body of the reagent injection catheter shown of FIG. 1.

As shown in FIGS. 2 and 3, of the above three holes (20, 22, 24) provided at the front end of the catheter body (10), the tip aperture (20) and side hole (24) are preferably arranged in such a way that their centers ($O_1$, $O_2$) are positioned in the plane ($\alpha$) that includes the center axes ($P_1$, $P_2$) of the first lumen (18a) and second lumen (18b). In accordance with preferred embodiments, the projection hole (22) is arranged in such a way that its center ($O_3$) is positioned in the aforementioned plane ($\beta$) that includes the center axis ($P_0$) of the catheter body (10) and that lies orthogonal to the plane ($\alpha$). This preferably allows the side hole (24) to open perpendicularly to the opening direction of the tip aperture (20) and to that of the projection hole (22).

In one preferred embodiment, the tip aperture (20) provided at the front end of the catheter body (10) connects to the first lumen (18a), the side hole (24) connects to the second lumen (18b), and the projection hole (22) connects to the third lumen (18c). This preferred configuration allows the first lumen (18a) to open in the forward axial direction (right direction in FIG. 1) through the tip aperture (20) at the front end of the catheter body (10). The second lumen (18b) preferably opens sideways through the side hole (24) perpendicularly to the opening direction of the first lumen (18a), while the third lumen (18c) opens through the projection hole (22) perpendicularly to both the opening directions of the first lumen (18a) and the second lumen (18b) (downward direction in FIG. 1).

In accordance with preferred embodiments of the present invention, three connectors (28, 30, 32) are attached to the catheter body (10) at its rear end as viewed in the insertion direction into the blood vessel (left side in FIG. 1). The connectors (28, 30, 32) are preferably attached via a branching socket (26), which branches the catheter body (10) into three parts. In addition, an insertion hole (34) that penetrates through the tubular wall of the catheter body (10) is preferably provided at a specified distance from the front of the installation position of the branching socket (26) at the rear end of the catheter body (10). The insertion hole preferably opens in the direction opposite to the opening direction of the aforementioned side hole (24), along the direction of the diameter of the catheter body (10).

The three connectors (28, 30, 32) each preferably connect to the second through fourth lumens (18b-18d) provided inside of the catheter. body (10). The insertion hole (34) also preferably connects to the first lumen (18a). This configuration preferably allows the first lumen (18a) to open outward through the insertion hole (34) at the rear end of the catheter body (10) as viewed in the insertion direction into the blood vessel, while allowing the second, third and fourth lumen (18b through 18d) to open outward through the three connectors (28, 30, 32).

In accordance with preferred embodiments, the needle tube (12) and first and second guide wires (14, 16) are inserted into the catheter body (10) to allow movement in their respective axial directions. The first guide wire (14) is preferably inserted into the first lumen (18a) provided in the catheter body (10) through the insertion hole (34) provided in the tubular wall at the rear end of the catheter body (10). The second guide wire (16) is preferably inserted into the second lumen (18b) provided in the catheter body (10) through the rear-end aperture opening in the connector (28) attached at the rear end of the catheter body (10). Further, the needle tube (12) is preferably inserted into the third lumen (18c) provided in the catheter body (10) through the opening in the connector (30) attached at the rear end of the catheter body (10).

As illustrated in FIGS. 1 and 3, which show the center axis positions of the needle tube (12) and guide wires (14, 16), the first guide wire (14) preferably moves in the forward axial direction inside of the first lumen (18a) and extends out of the first lumen (18a) in the forward axial direction within the aforementioned plane ($\alpha$) and through the tip aperture (20) at the front end of the catheter body (10). The second guide wire (16) preferably moves in the forward axial direction inside of the second lumen (18b), and extends out of the second lumen (18b) sideways within the aforementioned plane ($\alpha$) and through the side hole (24) at the front end of the catheter body (10). In accordance with preferred embodiments, the needle tube (12) moves in the forward axial direction inside of the third lumen (18c) and the tip of the needle (11) extends out of the third lumen (18c) perpendicular to both the extension direction of the first (14) and second guide wires (16), inside of the plane ($\beta$) orthogonal to the aforementioned plane ($\alpha$) and through the projection hole (22) at the front end of the catheter body (10).

The needle tube (12) which is inserted into the third lumen (18c) preferably comprises a flexible tube. A part of the needle tube (12), excluding the needle (11) at its tip, comprises a reagent flow channel (36) comprising a thin tube which is preferably longer than the catheter body (10) and which preferably comprises a diameter of approx 0.4 mm. In preferred embodiments, the needle tube (12) is continuous with the needle (11) and reagent flow channel (36).

The reagent flow channel (36) of the needle tube (12) preferably comprises a flexible composite resin material such as polytetrafluoroethylene or polyimide. The needle (11) preferably comprises an elastic alloy material such as Ni—Ti alloy, stainless steel, or other material known to those skilled in the art. The reagent flow channel (36), of the needle tube (12) is preferably connected to a syringe (38), which is attached to the connector (30) at the rear end of the catheter body (10) and which provides a reagent supplier for supplying a specified reagent.

Preferred structures of the needle tube (12) allows smooth insertion axial movement inside of the third lumen (18c) of the catheter body (10), which preferably has sufficient flexibility and/or elasticity for insertion into the winding blood vessel. The forward axial movement inside of the third lumeri (18c) causes the needle (11) to project out of the projection hole (22) of the catheter body (10) and pierce the myocardium. In particularly preferred embodiments, a reagent containing osteoblasts and/or growth factor for regenerating nearly or substantially dead cells of the myocardium, such as bFGF (basic Fibroblast Growth Factor), VEGF (Vascular Endothelial-cell Growth Factor) or HGF (Hepatic Growth Factor), can be introduced into the reagent flow channel (36) and discharged through the opening in the needle (11) by means of the syringe (38).

Figure 4:
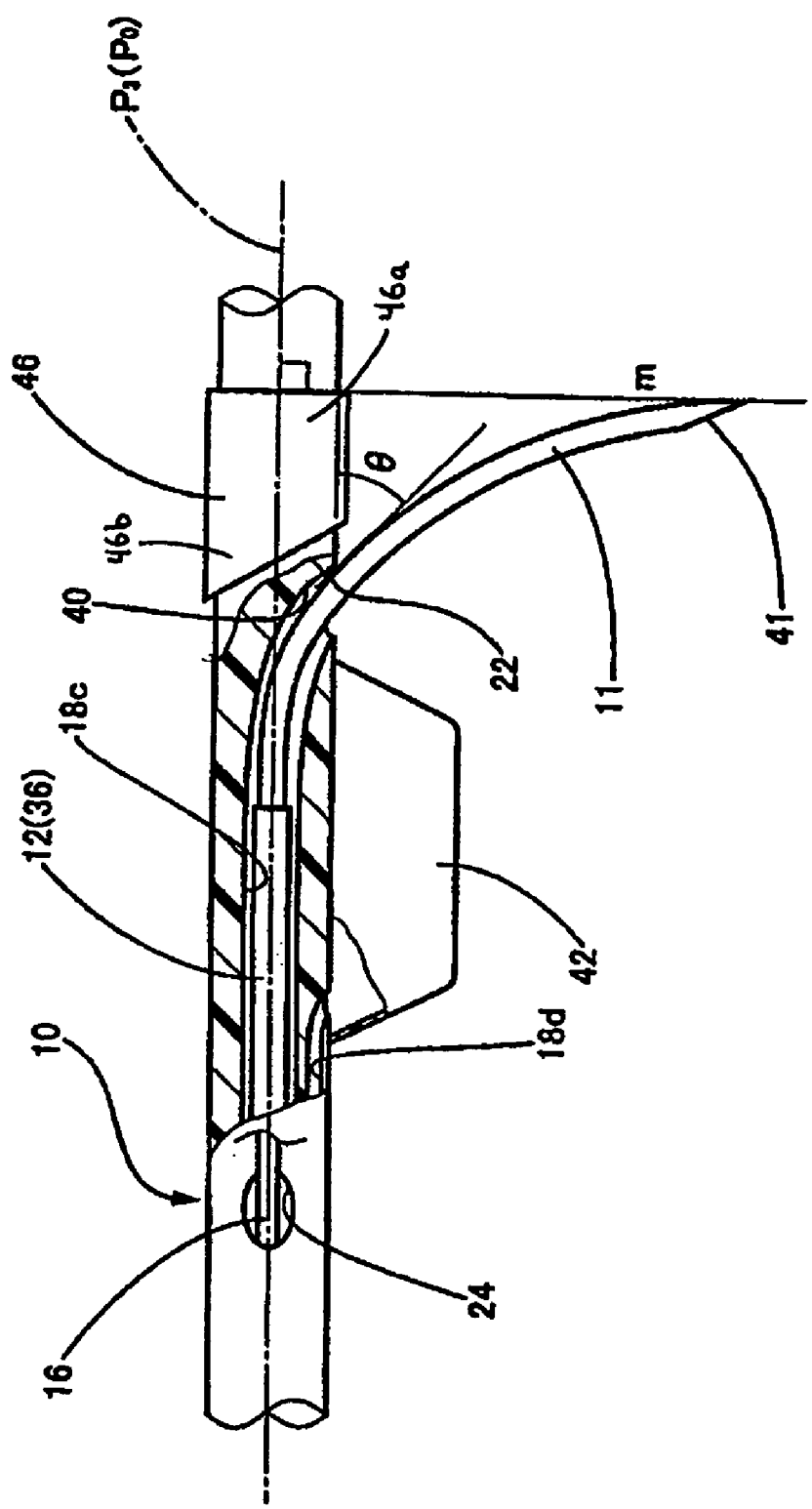
FIG. 4 shows an enlarged view, with the exterior wall partially removed to show the internal structure, of a portion of the reagent injection catheter of FIG. 1.

As illustrated in FIG. 4, the interior surface of the front end of the third lumen (18c), which includes the peripheral edge of the opening of the projection hole (22), preferably provides a guide surface (40) consisting of a convex curved surface curving in the forward axial direction toward the opening direction of the projection hole (22). In addition, the needle (11) of the needle tube (12) comprises a curved shape corresponding to the curved structure of the guide surface (40). This allows the needle (11) to be guided smoothly toward the projection hole (22) by the guide surface (40), through sliding contact with the guide surface (40), as the needle tube (12) moves in the forward axial direction.

Appropriate curved shapes of the guide surface (40) and needle (11) can preferably be determined by considering the stiffness of the needle (11). While the radius of curvature and other properties of the curved sections of the guide surface (40) and needle (11) are not specified herein, it is desirable that the projection angle (θ), which is formed at the contact point of the two sections when the curved pattern of the guide surface (40) is combined with the curved shape of the needle (11) when the needle (11) is projected out of the projection hole (22), is about forty-five degrees. In other preferred embodiments, the projection angle (θ) is more than forty-five degrees.

As shown in FIG. 4, the curved shapes of the guide surface (40) and needle (11) preferably allow the tip of the needle (11) to be positioned close to the projection hole (22) when the needle (11) is projected sufficiently out of the projection hole (22), thereby allowing the projecting position of the needle (11) to be easily identified. In addition, the tangential line (m) of the needle (11) can be caused to cross orthogonally, at a position closer to the projection hole (22), the center axis ($P_0$) of the catheter body (10) and the center axis ($P_3$) of the third lumen (18c) into which the needle tube (12) is inserted. As a result, the component force in the progressing direction of the needle tube (12) into the myocardium (of the two vectors Vv and Vh shown in FIG. 3, this component force corresponds to Vv, which is the vector perpendicular to the center axis ($P_3$) of the third lumen (18c)) will increase, thereby enabling the needle tube (12) to be inserted more smoothly into the myocardium.

Furthermore, the tip surface of the needle (11), namely the opening end face (41) of the opening in the needle (11), preferably provides an inclined surface facing the opening of the projection hole (22) when the needle (11) is projecting from the catheter body (10) (namely, the downward inclined surface shown in FIG. 4).

In preferred embodiments, a balloon (42) is provided between where the projection hole (22) and side hole (24) are formed at the front end of the catheter body (10). This balloon (42) preferably comprises a soft composite resin material and has a known structure that allows it to expand in the opening direction of the projection hole (22) when saline solution or other liquid is injected inside of the balloon. The balloon preferably shrinks from an extended state when such liquid is discharged. The fourth lumen (18d) preferably opens toward the inside of the balloon (42). As shown in FIG. 1, when being connected to the fourth lumen (18d), the connector (32) attached at the rear end of the catheter body (10) preferably has a syringe (44) connected thereto. The syringe (44) provides a means for supplying fluid to expand the balloon (42).

Figure 4A:
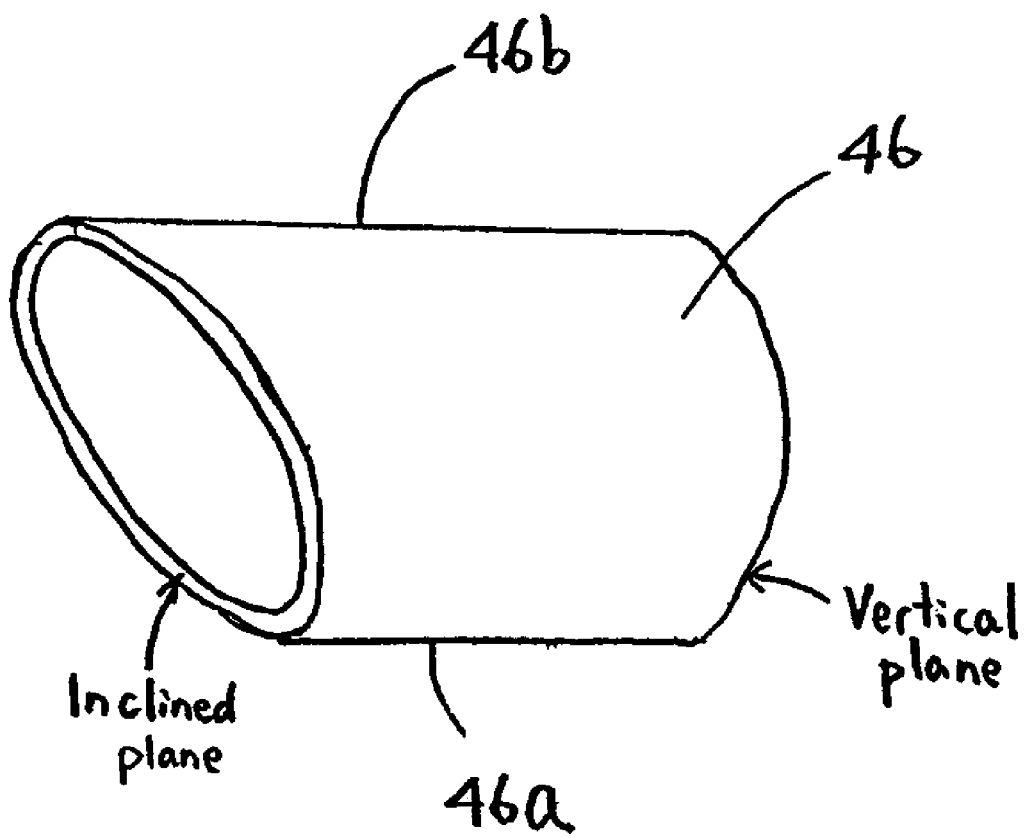
FIG. 4A shows a close-up view of the marker tube of FIG. 4.

In the preferred embodiments of FIGS. 1, 4 and 4A, a marker tube (46) can be made of a radio-opaque material such as gold, platinum or platinum-rhodium alloy. Preferred embodiments of the marker tube (46) have an inclined opening end face on one side of the axial direction, with the longest and shortest sections (46b, 46a) in the axial direction formed along the cylinder wall. This marker tube (46) is preferably inserted over the front end of the catheter body (10) and is preferably fixed at a position where either the longest or shortest sections (46b, 46a) of the cylinder wall corresponds to the position of the projection hole (22) at the front end of the catheter body (10). The tip of the marker tube (46) preferably corresponds to the tangential line (m) of the needle tube (12) (needle (11)) when the needle tube (12) is projected. This allows the position of the projection hole (22) and that of the tip of the needle tube (12), in a condition where the catheter body (10) is inserted into the blood vessel, to be identified easily through an X-ray fluoroscopy of the tip, the longest section (46b), and the shortest section (46a) of the cylinder wall of the marker tube (46). In the preferred embodiment shown in FIG. 4, the shortest section (46a) of the cylinder wall of the marker tube (46) is preferably positioned on the side which comprises the projection hole (22).

Embodiments of the present invention further comprise methods of injecting a specified reagent into tissue, such as a nearly or substantially necrosis tissue or other lesion in the myocardium, using a reagent injection catheter of the present invention.

Figure 5:
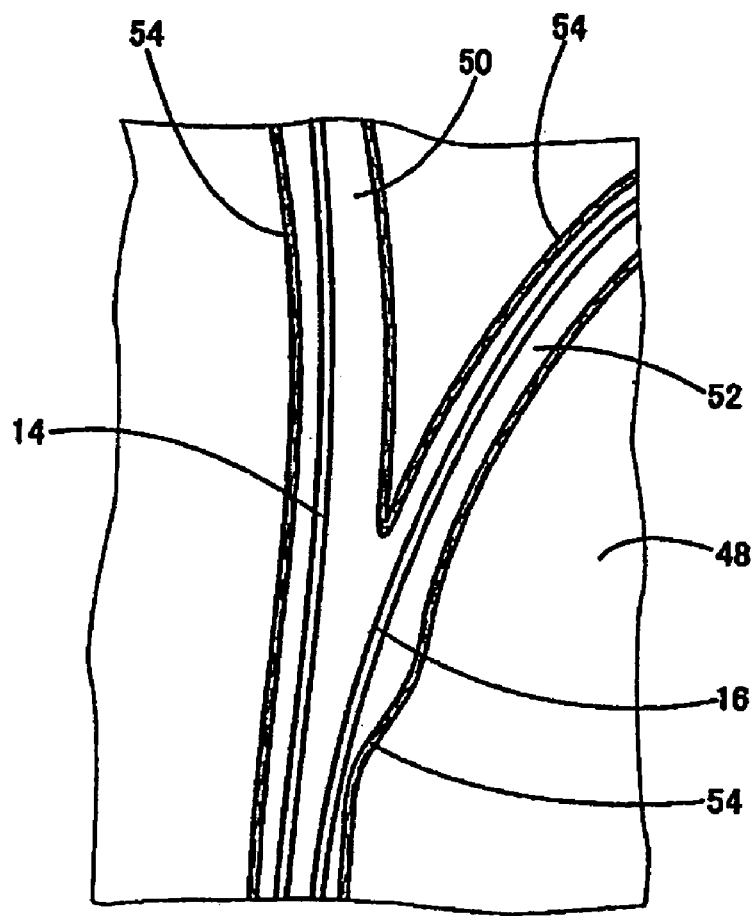
FIG. 5 shows injection of a specified reagent into a lesion in the myocardium using the reagent injection catheter shown in FIG. 1, further illustrating the condition of the first guide wire and second guide wire inserted into the main blood vessel and branch blood vessel, respectively, at the surface of the myocardium.

When implementing a reagent injection therapy using such a reagent injection catheter, the first guide wire (14) is preferably inserted into the main blood vessel (50) at the surface of the myocardium (48), as shown in FIG. 5. The second guide wire (16) is preferably inserted into the branch blood vessel (52) at the surface of the myocardium (48), which is branching from the main blood vessel (50) in which the first guide wire (14) is inserted. In some preferred embodiments, the insertion operations of the first and second guide wires (14, 16) into the main blood vessel (50) and branch blood vessel (52) can be performed manually.

The catheter body (10) is then preferably inserted into the main blood vessel (50) at the surface of the myocardium (48), along the first guide wire (14). This insertion operation of the catheter body (10) into the main blood vessel (50) is preferably performed while checking, using X-ray fluoroscopy and a monitor or other means known to those skilled in the art, the position of the marker tube (46) inserted over the front end of the catheter body (10) as viewed in the insertion direction. When the marker tube (46) reaches a specified position in the main blood vessel (50), as the catheter body (10) progresses into the main blood vessel (50), the insertion operation of the catheter body (10) can be temporarily stopped. The positions of the shortest section (46a) and longest section (46b) of the marker tube (46) are then preferably checked, and the catheter body (10) rotated around its axis so that the projection hole (22) opens toward the specified position in the lesion in the myocardium (48) into which the reagent will be injected. The axial-direction position of the catheter body in the blood vessel (50) can be simultaneously adjusted.

Figure 6:
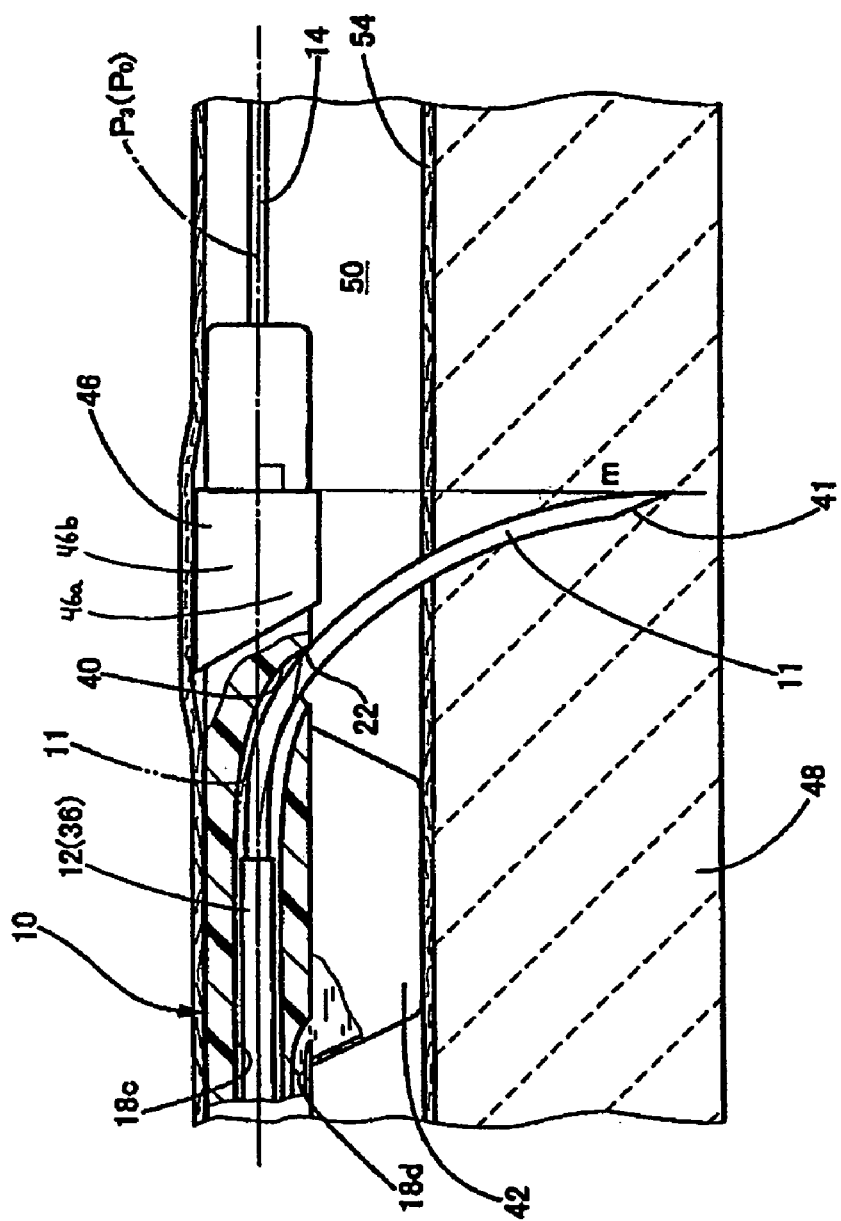
FIG. 6 shows another example of injecting a specified reagent into a lesion in the myocardium using the reagent injection catheter shown in FIG. 1, illustrating the condition of the needle pierced into the myocardium.

When the catheter body (10) reaches the aforementioned specified position in the main blood vessel (50), as shown in FIG. 6, saline solution or other liquid can be introduced from the syringe (44) into the fourth lumen (18d) inside the catheter body (10) to expand the balloon (42) toward the opening direction of the projection hole (22). This preferably fixes the catheter body (10) inside the main blood vessel (50) over the lesion in the myocardium (48) into which the reagent will be injected.

Next, the needle tube (12) is preferably inserted into the third lumen (18c) in the catheter body (10) through the connector (30), and is moved forward in the insertion direction of the catheter body (10) into the main blood vessel (50). Once the needle (11) at the tip of the needle tube (12) reaches the front end of the third lumen (18c), the needle (11) can progress forward smoothly toward the projection hole (22) by means of sliding contact with the guide surface (40) provided on the interior surface of the third lumen (18c) at the front end, as shown by the two-dot chain line in FIG. 6. By this further forward movement of the needle tube (12), the needle (11) is preferably caused to project out of the projection hole (22), as shown by the solid line in FIG. 6. This projection operation of the needle (11), by means of the movement of the needle tube (12), can preferably be performed manually or by using a known screw mechanism known by those skilled in the art.

Preferred embodiments of the reagent injection catheter allow the needle (11) of the needle tube (12) to be projected out of the projection hole (22) in a direction virtually perpendicular to the extension direction of the first guide wire (14), which extends out of the tip aperture (20) in the catheter body (10). Preferred embodiments of the reagent injection catheter also allow the needle (11) of the needle tube (12) to be projected out of the projection hole (22) in a direction virtually perpendicular to the extension direction of the second guide wire (16), which extends out of the side hole (24) in the catheter body (10). The first guide wire (14) is inserted into the main blood vessel running at the surface of the myocardium (48), and the second guide wire (16) is inserted into the branch blood vessel (52) which also runs at the surface of the myocardium (48). Thus, the surface formed by the first and second guide wires (14, 16) virtually approximates the surface of the myocardium (48).

The needle (11) of the needle tube (12) projecting out of the projection hole (22) in the catheter body (10) via the aforementioned operation will preferably project in the direction virtually perpendicular to the surface of the myocardium (48). Furthermore, the curved shape of the needle (11), which is curved in the projection direction out of the projection hole (22) in the moving direction of the needle tube (12), preferably allows the tangential line (m) at the tip to cross orthogonally the center axis ($P_0$) of the catheter body (10) when the needle is projecting out of the projection hole (22). The term "virtually perpendicular" is used here because, since the myocardium (48) actually has a complex shape, in the strict sense the needle (11) may not always project perpendicularly to the surface of the myocardium (48).

In preferred embodiments, the needle (11) of the needle tube (12) projecting out of the projection hole (22) in the catheter body (10) will pierce through the vascular wall (54) of the main blood vessel (50) to reach the specified position in the lesion in the myocardium (48). As the needle tube (12) moves forward in the catheter body (10), the needle (11) will progress in a direction virtually perpendicular to the surface of the myocardium (48) to reach the specified depth in the lesion.

When the needle (11) progresses into the lesion, a majority of the reactive force generated in response to the progress of the needle (11) into the myocardium (48) will act on the catheter body (10) in the direction opposite to the progressing direction of the needle (11), or, the direction perpendicular to the surface of the myocardium (48). However, the first guide wire (14) and second guide wire (16) can be inserted into the main blood vessel (50) and branch blood vessel (52), respectively, at the surface of the myocardium (48). Therefore, such reactive force can be divided and each component force can be sufficiently and reliably supported by the first and second guide wires. This operation preferably allows the needle to progress to a specified depth in the lesion in the myocardium (48) in a smooth and reliable manner.

In accordance with preferred embodiments, when the needle (11) reaches the desired depth in the lesion in the myocardium (48), the movement of the needle tube (12) will be terminated. Thereafter, a reagent containing osteoblast and/or growth factor, or other reagent known to those skilled in the art, to regenerate the myocardium (48) can be introduced into the internal hole of the needle tube (12) via the syringe (44) connected to the connector (32) at the basal position of the needle tube (12). Such a reagent is preferably discharged from the tip aperture of the needle (11) and injected into the lesion in the myocardium (48).

Thereafter, when the reagent is injected into one location of lesion in the myocardium (48), the needle tube (12) can be preferably retracted within the catheter body (10), and the needle (11) pulled into the catheter body (10). This reagent injection operation at a lesion in the myocardium (48) can preferably be repeated multiple times, thereby allowing the reagent to be injected into multiple lesions in the myocardium (48).

The needle (11) projecting out of the projection hole (22) in the catheter body (10) preferably pierces a specified position in the lesion in the myocardium (48) in a reliable manner. In addition, a majority of the reactive force generated by such piercing of the myocardium (48) by the needle (11) can be sufficiently and reliably supported by the first guide wire (14) and second guide wire (16) inserted into the main blood vessel (50) and branch blood vessel (52), respectively, at the surface of the myocardium (48). This allows the needle (11) to preferably progress into a specified depth at the lesion in the myocardium (48) in a very smooth and reliable manner.

Thus, by using such a reagent injection catheter of this example, the needle (11) will preferably pierce through to a desired depth at a specified position in the lesion in the myocardium (48), even when the lesion has been hardened. This further and sufficiently increases the effect of the treatment or procedure to inject into the lesion in the myocardium (48) a reagent for regenerating the myocardium (48).

In preferred embodiments, the first through fourth lumens (18a through 18d) are provided independently inside the catheter body (10) in a manner extending continuously in the longitudinal direction of the catheter body (10). The first, second and third lumens (18a through 18c) preferably contain the first and second guide wires (14, 16) and needle tube (12), respectively, in a manner which allows movement in the axial direction. This configuration allows the first and second guide wires (14, 16) and needle tube (12) to smoothly move in the axial direction inside the catheter body (10). Consequently, a smoother implementation of the applicable medical technique becomes possible.

Furthermore, in embodiments of the present invention, the first guide wire (14) is inserted into the first lumen (18a) through an insertion hole (34) that opens to the side at the rear end of the catheter body (10), and extends straight in the forward axial direction via the tip aperture (20) in the catheter body (10). Additionally, the second guide wire (16) is inserted straight into the second lumen (18b) through the opening in the connector (26) attached at the rear end of the catheter body (10), and extends sideways via the side hole (24) that opens to the side at the front end of the catheter body (10).

In preferred reagent injection catheters both the first guide wire (14) and second guide wire (16) preferably pass through the catheter body (10) in a condition that is bent or curved at only one location. Therefore, when the catheter body (10) is inserted into the main blood vessel (50) at the surface of the myocardium (48) along the first and second guide wires (14, 16), the guide wires (14, 16) will experience relatively small slide resistance, thus allowing for a smoother insertion of the catheter body (10) into the main blood vessel (50).

The third lumen (18c), into which the needle tube (12) is inserted, can be preferably arranged so that its center axis ($P_3$) corresponds to the center axis ($P_0$) of the catheter body (10). This ensures a good overall balance of the reagent injection catheter and enables the applicable medical technique for injecting a reagent into a lesion in the myocardium (48) to be performed in a more stable manner.

In preferred embodiments of the reagent injection catheter the projection hole (22) is arranged so that the center ($O_3$) of the projection hole (22), through which the needle (11) of the needle tube (12) projects, is positioned in the plane ($\beta$) lying orthogonal to the plane ($\alpha$) that includes the center axis ($P_3$) of the third lumen (18c) into which the needle tube (12) is inserted, the corresponding center axis ($P_0$) of the catheter body (10), and the center axes ($P_1$, $P_2$) of the first and second lumens (18a, 18b) into which the first and second guide wires (14, 16) are inserted. This allows a preferable layout balance of the needle tube (12) inside of the catheter body (10), and a good balance when the needle (11) is projected out of the projection hole (22). As a result, the applicable medical technique to inject a reagent into a lesion in the myocardium (48) can be performed in a more stable and smoother manner.

In preferred embodiments the center axes ($P_1$, $P_2$) of the first and second lumens (18a, 18b), into which the first and second guide wires (14, 16) are inserted, are positioned in the aforementioned single plane ($\alpha$) together with the center axis ($P_0$) of the catheter body (10) and the center axis ($P_3$) of the third lumen (18c) into which the needle tube (12) is inserted. Moreover, the first and second lumens (18a, 18b) can be preferably located on both sides of the third lumen (18c). This configuration preferably maximizes the distance between the first lumen (18a) and second lumen (18b), thereby increasing the distance between the first guide wire (14) and second guide wire (16) extending out form these two lumens (18a, 18b) through the tip aperture (20) and side hole (24) in the catheter body (10), respectively. As a result, a majority of the reactive force generated as the needle (11) progresses into the lesion in the myocardium (48) can be supported by the first guide wire (14) and second guide wire (16).

In accordance with preferred embodiments, the fourth lumen (18d) that supplies the liquid for expanding the balloon (42) is positioned in such a way that its center axis ($P_4$) is positioned in the aforementioned plane ($\beta$) that includes the center axis ($P_3$) of the third lumen (18c) into which the needle tube (12) is inserted, the center axis ($P_0$) of the catheter body, and the center ($O_3$) of the projection hole (22). This configuration preferably ensures a good overall balance of the reagent injection catheter, thus allowing the applicable medical technique for injecting a reagent into a lesion in the myocardium (48) to be performed in a more stable manner.

The interior surface at the front end of the third lumen (18c), into which the needle tube (12) is inserted, preferably provides a guide surface (40) consisting of a convex curved surface curving in the opening direction of the projection hole (22) in the forward axial direction. Additionally, the needle (11) of the needle tube (12) is also preferably formed with a curved shape corresponding to the guide surface (40). Therefore, as the needle tube (12) moves forward inside the catheter body (10), the needle (11) will preferably project out of the projection hole (22) in a direction perpendicular to the surface of the myocardium (48). This structure also allows the applicable medical technique for injecting a reagent into a lesion in the myocardium (48) to be performed in a more stable and reliable manner.

Preferred embodiments provide various possible configurations of the positions of the first through fourth lumens (18a through 18d) provided within the catheter body (10). For example, as shown in FIG. 7 the third lumen (18c) can be preferably arranged so that its center axis ($P_3$) deviates from the center axis ($P_0$) of the catheter body (10) toward the projection hole (22) along the diameter direction of the catheter body (10), while the first and second lumens (18a, 18b) can be arranged in such a way that the plane ($\alpha$) including their respective center axes ($P_1$, $P_2$) deviates from the center axis ($P_0$) of the catheter body (10) toward the opposite direction of the projection hole (22) along the diameter direction of the catheter body (10).

Figure 8:
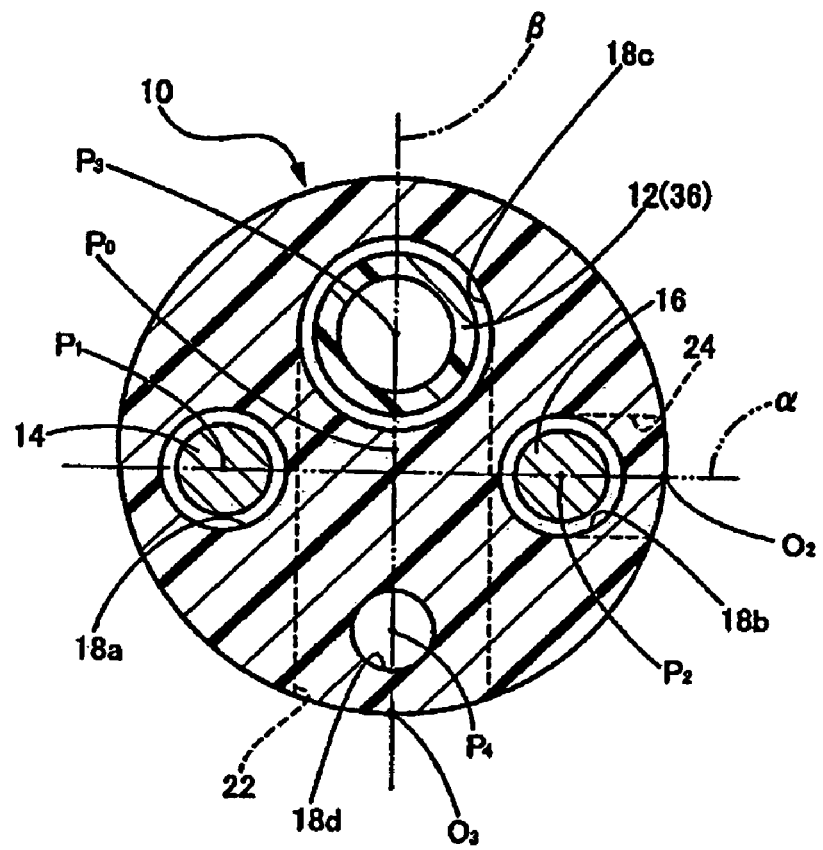
FIG. 8 shows a cross-sectional view of another example of a reagent injection catheter.

Moreover, as shown in FIG. 8, the third lumen (18c) can preferably be arranged in such a way that its center axis ($P_3$) deviates from the center axis ($P_0$) of the catheter body (10) toward the opposite direction of the projection hole (22) along the diameter direction of the catheter body (10). The first and second lumens (18a, 18b) can simultaneously be arranged in such a way that the plane ($\alpha$), including their respective center axes ($P_1$, $P_2$), deviates from the center axis ($P_0$) of the catheter body (10) toward the projection hole (22) along the diameter direction of the catheter body (10).

Figure 7:
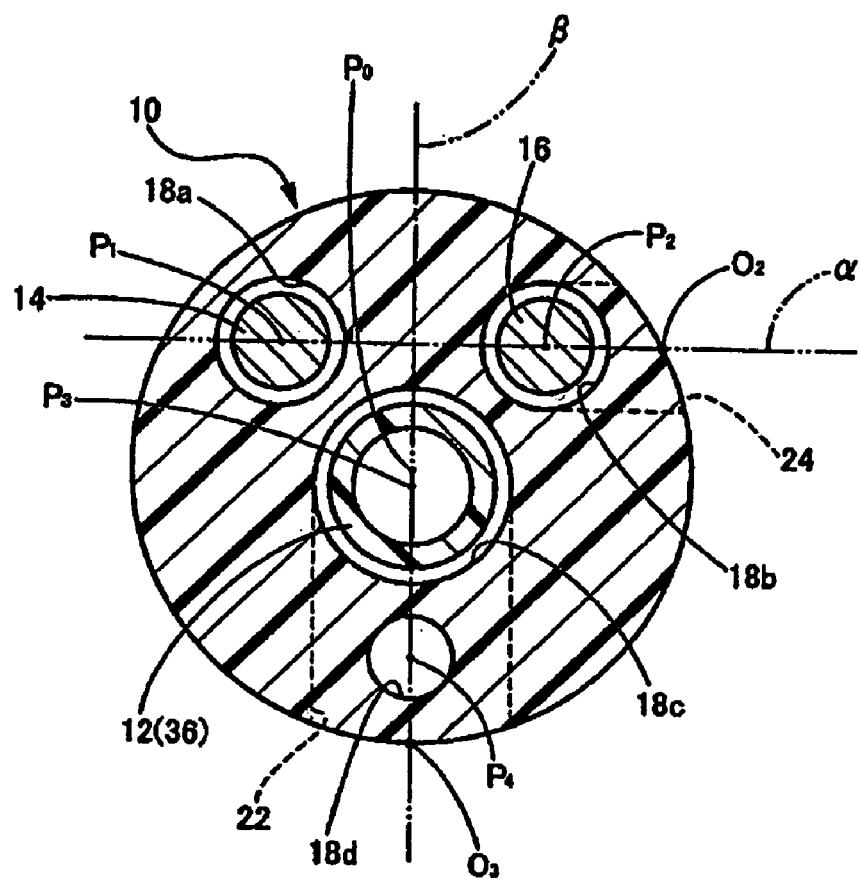
FIG. 7 shows a cross-sectional view of another example of a reagent injection catheter.

In the two embodiments shown in FIGS. 7 and 8, the needle (11) of the needle tube (12) is projected in a direction perpendicular to the extension directions of the first and second guide wires (14, 16). Therefore, these second and third examples can function similarly to the previously described embodiments.

Figure 9:
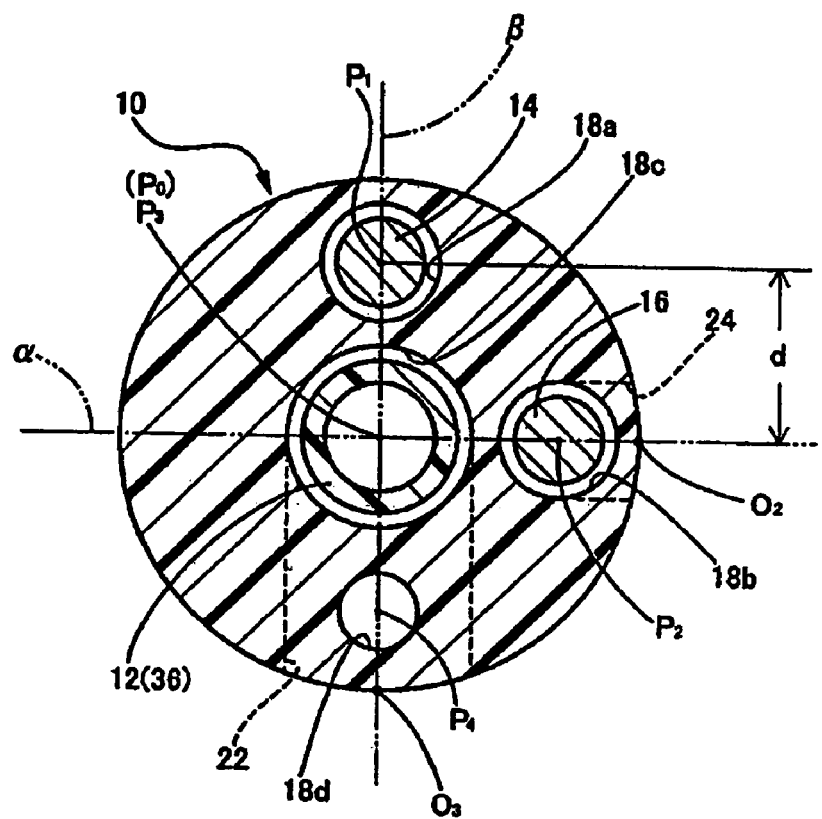
FIG. 9 shows a cross-sectional view of another example of a reagent injection catheter.

As shown in FIG. 9, the third lumen (18c) can preferably be arranged coaxially to the catheter body (10), while the first lumen (18a) can be arranged in such a way that its center axis ($P_1$) is positioned on the opposite side of the center ($O_3$) of the projection hole (22) across the center axis ($P_3$) of the third lumen (18c) inside the plane ($\beta$) that includes the center axis ($P_3$) of the third lumen (18c), the center axis ($P_0$) of the catheter body (10) and the center ($O_3$) of the projection hole (22). The second lumen (18b) can then preferably be arranged in such a way that its center axis ($P_2$) is positioned in the plane ($\alpha$) that lies orthogonally to the above plane ($\beta$), and includes the center axis ($P_3$) of the third lumen (18c), and the center axis ($P_0$) of the catheter body (10).

Figure 10:
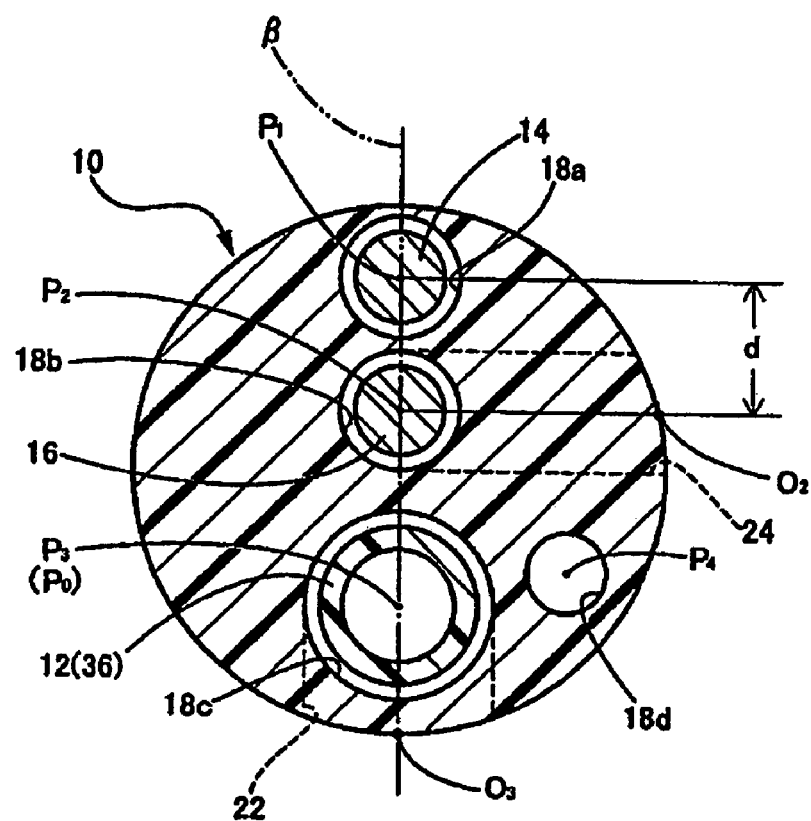
FIG. 10 shows a cross-sectional view of another example of a reagent injection catheter.

Furthermore, as shown in FIG. 10, the first, second and third lumens (18a through 18c) can be arranged in such a way that their center axes ($P_1$ through $P_3$) are positioned in the aforementioned plane ($\beta$) that includes the center axis ($P_0$) of the catheter body (10) and the center ($O_3$) of the projection hole (22). The fourth lumen (18d) can also be arranged in a position different from those in the first through third examples explained above.

In the embodiments shown in FIGS. 9 and 10, the first lumen (18a) and second lumen (18b) are displaced and parallel with each other, and the positions of their respective center axes ($P_1$, $P_2$) have a deviation (d) in the diameter direction of the catheter body (10). However, such deviation (d) is minute, and is preferably smaller than the diameter of the catheter body (10). Therefore, the extension-direction vectors of the first and second guide wires (14, 16), which are inserted into these first and second lumens (18a, 18b), still preferably cross each other, and thus the needle tube (12) can virtually project onto the plane that includes these vectors. Thus, in preferred embodiments little impact is caused by the minute deviation (d).

In accordance with preferred embodiments of FIGS. 9 and 10, the needle (11) of the needle tube (12) preferably projects in a direction virtually perpendicular to the extension directions of the first and second guide wires (14, 16).

Further preferred embodiments of the reagent injection catheter of the present invention provide numerous structural variations. For example, the balloon (42) provided externally to the catheter body (10), and the fourth lumen (18*d*) provided in the catheter body (10) to supply the liquid for expanding such a balloon (42), can be omitted from some embodiments. Of course, in the event that the balloon (42) and fourth lumen (18*d*) are to be provided, their positions and quantities should not be limited to those in the aforementioned examples. Other preferred embodiments comprise a guide surface (40) comprising a convex curved surface on the interior surface at the front end of the third lumen (18*c*), and comprise a needle (11) having a straight shape.

Furthermore, while in the aforementioned examples the opening end face (41) of the needle (11) provides an inclined surface (downward inclined surface in FIG. 1) that slopes in the projection direction of the needle (11), toward the moving direction of the needle tube (12) when the needle (11) projects out of the projection hole (22), preferred embodiments can alternatively comprise an opening end face (41) that can be provided as an inclined surface (upward inclined surface in FIG. 1) that slopes in the projection direction of the needle (11) toward the opposite direction to the moving direction of the needle tube (12) when the needle (11) projects out of the projection hole (22). In certain embodiments, an opening end face (41) which comprises a downward inclined surface (see FIG. 1) can preferably prevent the interior surface of the third lumen (18*c*) from being scratched or damaged due to contact with the needle (11), which might otherwise occur as the needle (11) moves inside the third lumen (18*c*).

Preferred embodiments of the present invention, including but not limited to the aforementioned embodiments, can also be used for injecting a reagent into tissues other than the myocardium. Moreover, preferred embodiments of the present invention can also apply to non-catheter reagent injection devices for injecting a reagent into myocardium lesions or other tissues known to those skilled in the art.

The present invention can be embodied with various changes, modifications or improvements added based on the knowledge of those skilled in the art, although specific examples of such changes, modifications and improvements are not listed here. Of course, such embodiments are included in the scope of the present invention unless they deviate from the purpose of the present invention.

What is claimed is:

1. A reagent injection device comprising:
   a flexible main tube, which is insertable into a body, said main tube comprising first, second, and third lumens provided therein, said third lumen being disposed closer to an axial center of the main tube than are the first and second lumens;
   a first guide wire that is insertable into the main tube through the first lumen and which is configured to guide the first guide wire to move back and forth by extending out of the main tube at a first position in an axial direction of the main tube;
   a second guide wire that is insertable into the main tube through the second lumen which is configured to guide the second guide wire to move back and forth by extending out of the main tube at a second position in a direction away from the first guide wire, wherein the first guide wire and the second guide wire are extendable from the main tube on a common plane with reference to the extended first guide wire and the extended second guide wire, said common plane being formed by the extended first guide wire and the extended second guide wire and extending through the extended first guide wire, the extended second guide wire, and the main tube; and
   a needle tube that is insertable into the main tube through the third lumen and which is configured to guide the needle tube to move back and forth by projecting from the main tube at a third position in a direction substantially or nearly orthogonal to the common plane and away from the common plane by using the first and second guide wires on the common plane as a support structure, said third position being disposed between the first position and the second position in the axial direction of the main tube,
   wherein the main tube further comprises an expandable and/or shrinkable balloon attached to its exterior, and a fourth lumen that supplies fluid for expanding the balloon is further provided inside of the main tube such that the center of the projection hole is positioned in the same plane that includes the center axis of the fourth lumen and the center axis of the main tube.

2. A reagent injection device as described in claim 1, wherein
   the first lumen opens to the outside through a tip aperture of the main tube which is the first position;
   the second lumen opens to the outside through a side hole which is the second position; and
   the third lumen opens to the outside through a projection hole which is the third position, wherein the first guide wire is inserted into the first lumen, the second guide wire is inserted into the second lumen, and the needle tube is inserted into the third lumen in a manner that allows axial movement.

3. A reagent injection device as described in claim 2, wherein the first lumen opens to the side through an insertion hole provided in the tubular wall at the rear end of the main tube as viewed in the direction of its insertion into the body, wherein the first guide wire is inserted into the first lumen through the insertion hole, the second lumen opens to the rear through a rear-end aperture at the rear of the main tube, and the second guide wire is inserted into the second lumen through the rear-end aperture.

4. A reagent injection device as described in claim 2, wherein the first and second lumens are provided inside of the main tube such that the plane that includes the center axes of the lumens lies orthogonal to the opening direction of the projection hole.

5. A reagent injection device as described in claim 2, wherein the third lumen is provided inside the main tube such that the center of the projection hole is positioned in the plane that includes the center axis of the third lumen and the center axis of the main tube.

6. A reagent injection device as described in claim 2, wherein the third lumen is provided inside the main tube such that its center axis corresponds to the center axis of the main tube, and wherein the first and second lumens are provided inside the main tube on both sides of the third lumen such that their center axes are positioned in the same plane that includes the center axis of the third lumen.

7. A reagent injection device as described in claim 1, wherein the main tube further comprises a guide surface that guides the needle into the projection hole by means of sliding contact made by the needle along with the axial movement of the needle tube, wherein the guide surface comprises a convex curve that curves in the opening direction of the projection hole toward the front of the main tube as viewed in the direction of its insertion into the body.

8. A reagent injection device as described in claim 7; wherein the needle comprises a curve corresponding to the curved guide surface, and wherein the needle tube is caused to deform in a manner creating a deeper curve by combining the convex curved shape of the guide surface and the curved shape of the needle.

9. The reagent injection device as described in claim 1, further comprising a reagent supplier configured to supply reagent through the needle tube.

10. A method of injecting a reagent into a human body, comprising:
inserting into a human body a tubular body which comprises a main tube and a projection hole on its exterior, said main tube comprising first, second, and third lumens provided therein, said third lumen being communicated with the projection hole and disposed closer to an axial center of the main tube than are the first and second lumens;
inserting an axially-moveable first guide wire into the main tube through the first lumen, wherein the first guide wire extends through a tip aperture provided at the front of the main tube as viewed in the direction of its insertion into the body;
inserting an axially moveable second guide wire into the main tube through the second lumen, wherein the second guide wire extends through a side hole that opens in a direction such that the first and second guide wires are extended from the main tube on a common plane with reference to the extended first guide wire and the extended second guide wire, said common plane being formed by the extended first guide wire and the extend second guide wire, extending through the extended first guide wire, the extended second guide wire, and the main tube, and being substantially or nearly orthogonal to an opening direction of the projection hole which is disposed between the tip aperture and the side hole in an axial direction of the main tube;
inserting an axially-moveable needle into the main tube through the third lumen;
guiding the needle to a tissue in the body with the first and second guide wires;
projecting the needle through the projection hole and into the tissue in a direction substantially or nearly orthogonal to the common plane and away from the common plane by using the first and second guide wires on the common plane as a support structure;
supplying a specified reagent into the needle tube; and injecting reagent into the tissue.

11. A reagent injection device for injecting a reagent into a human body, comprising:
a tubular body configured to be inserted into a human body and comprising a main tube having (a) a tip aperture provided at a distal end, (b) a projection hole provided on a side, and (c) a side hole provided on a side, wherein the projection hole is disposed between the tip aperture and the side hole in an axial direction of the main tube, said main tube comprising a first lumen communicated with the tip aperture, a second lumen communicated with the side hole, and a third lumens communicated with the projection hole and disposed closer to an axial center of the main tube than are the first and second lumens;
an axially-moveable first guide wire that is inserted into the tubular body through the first lumen and that is configured to extend through the tip aperture in an axial direction of the tubular body; and
an axially-moveable second guide wire that is inserted into the tubular body through the second lumen and that is configured to extend through the side hole in a direction such that when the first and the second guide wires extend, the first and the second guide wires define a common plane with reference to the extended first guide wire and the extended second guide wire, said common plane being formed by the extended first guide wire and the extended second guide wire and extending through the extended first guide wire, the second extended guide wire, and the main tube;
an axially-moveable needle tube for injecting a reagent which is formed with a thin flexible tube, wherein the needle tube is inserted into the tubular body through the third lumen and is configured to project through the projection hole in a direction substantially or nearly orthogonal to the common plane,
wherein when the tubular body is inserted into the body, the needle projects through the projection hole and pierces tissue in the body in the direction substantially or nearly orthogonal to the common plane and away from the common plane by using the first and second guide wires on the common plane as a support structure, and a reagent can be supplied through the needle tube and injected into the tissue.

12. The reagent injection device according to claim 11, wherein the tubular body is provided with a marker in the vicinity of the projection hole, which marker is made of a radiopaque material.

13. The reagent injection device according to claim 11, wherein the tubular body has a curved guide surface that leads the needle to the projection hole when the needle is inserted into the tubular body, said curved guide surface being configured to guide the needle to project from the projection hole at an angle of no less than about 45° but less than about 90° with respect to the axis of the tubular body to allow the tip of the needle to extend in a direction generally orthogonal to the plane.

14. The reagent injection device according to claim 11, wherein the first lumen and the second lumen are generally parallel to each other in the tubular body.

15. The reagent injection device according to claim 14, wherein the first and the second lumens are arranged in the tubular body to maximize a distance between an axis of the first lumen and an axis of the second lumen.

16. The reagent injection device as described in claim 11, further comprising a reagent supplier configured to supply reagent through the needle tube.

* * * * *